(12) United States Patent
Hestad et al.

(10) Patent No.: US 8,641,609 B2
(45) Date of Patent: Feb. 4, 2014

(54) SURGICAL ACCESS SYSTEM AND METHOD OF USING THE SAME

(75) Inventors: Hugh D. Hestad, Edina, MN (US); Robert G. Hudgins, Monticello, MN (US); John Dawson, Chaska, MN (US); Chris Hrabe, Eden Prairie, MN (US); Thomas O. Viker, Arden Hills, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1869 days.

(21) Appl. No.: 11/877,231

(22) Filed: Oct. 23, 2007

(65) Prior Publication Data

US 2009/0105546 A1     Apr. 23, 2009

(51) Int. Cl.
    *A61B 1/32*     (2006.01)

(52) U.S. Cl.
    USPC ............................. 600/205; 600/212; 600/215

(58) Field of Classification Search
    USPC ......... 600/205, 201, 212, 214, 219, 245, 187, 600/156–159, 200; 128/DIG. 27; 62/259.3, 62/293; 165/80.1, 80.5, 168–170, 154; 606/162
    See application file for complete search history.

(56) References Cited

U.S. PATENT DOCUMENTS

| | | | |
|---|---|---|---|
| 3,882,855 A * | 5/1975 | Schulte et al. | 600/206 |
| 5,019,038 A * | 5/1991 | Linden | 604/540 |
| 5,743,852 A * | 4/1998 | Johnson | 600/207 |
| 5,792,044 A | 8/1998 | Foley et al. | |
| 5,944,711 A * | 8/1999 | Pender | 604/514 |
| 6,458,094 B1 * | 10/2002 | McMahon et al. | 604/35 |
| 6,504,985 B2 | 1/2003 | Parker et al. | |
| 6,733,442 B1 * | 5/2004 | Larnard | 600/203 |
| 7,150,714 B2 | 12/2006 | Myles | |
| 2004/0181231 A1 | 9/2004 | Emstad et al. | |
| 2006/0235279 A1 | 10/2006 | Hawkes et al. | |
| 2008/0185924 A1 * | 8/2008 | Masoudipour et al. | 310/54 |

OTHER PUBLICATIONS

Teuvo Sihvonen et al; Local Denervation Atrophy of Paraspinal Muscles in Postoperative Failed Back Syndrome; SPINE; copyright 1993; pp. 575-581; vol. 18, No. 5; J.B. Lippincott Company.

Jorma R. Styf, M.D., et al.; The Effects of External Compression by Three Different Retractors on Pressure in the Erector Spine Muscles During and After Posterior Lumbar Spine Surgery in Humans; SPINE; copyright 1998, pp. 354-358; vol. 23, No. 3; Lippincott-Raven Publishers.

(Continued)

*Primary Examiner* — Eduardo C Robert
*Assistant Examiner* — Julianna N Harvey
(74) *Attorney, Agent, or Firm* — Seager, Tufte & Wickhem, LLC

(57) ABSTRACT

A method of thermally treating tissue during a surgical procedure where a surgical access device, including a body member having walls with at least one conduit therein, is inserted into the patient. A chilled fluid is circulated through the at least one conduit such that the tissue that is located proximate the body member is cooled. Alternatively, the body member may be constructed from a highly thermally conductive material such that heat energy is transmitted through the body from the tissue located proximate the body member and into a heat sink. The surgical device may include a first or second blade portions constructed from an inner and an outer shell having walls. Ribs located on the inner shell sealingly coupled to the inner wall of the outer shell to create the at least one conduit within the walls of the blade portion.

12 Claims, 10 Drawing Sheets

(56) References Cited

OTHER PUBLICATIONS

Yoshiharu Kawaguchi, M.D., et al.; Back Muscle Injury After Posterior Lumbar Spine Surgery-Topographic Evaluation of Intramuscular Pressure and Blood Flow in the Porcine Back Muscle During Surgery; SPINE; copyright 1996; pp. 2683-2688; vol. 21; No. 22; Lippincott-Raven Publishers.

Ramon M. Esclamado, MD., et al; Effect of Local Hypothermia on Early Wound Repair; Arch Otolaryngol Head Neck Surg.; Jul. 1990; pp. 803-808; vol. 116.

* cited by examiner

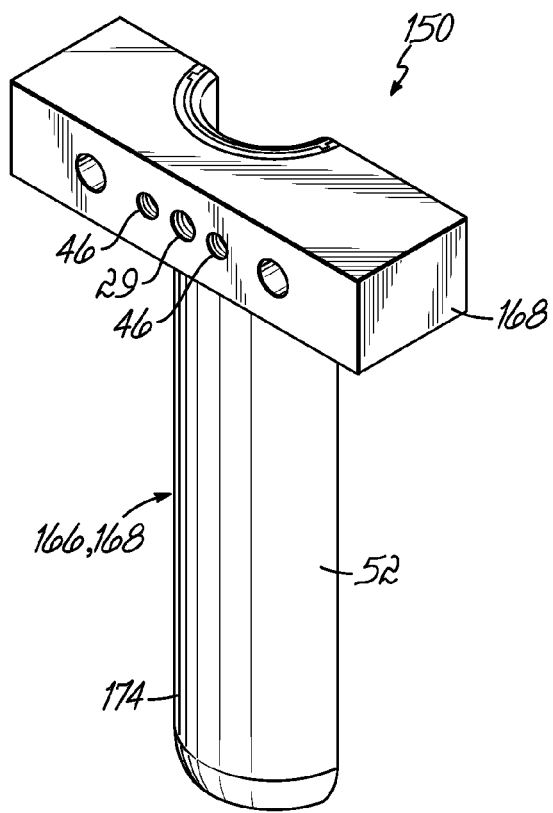
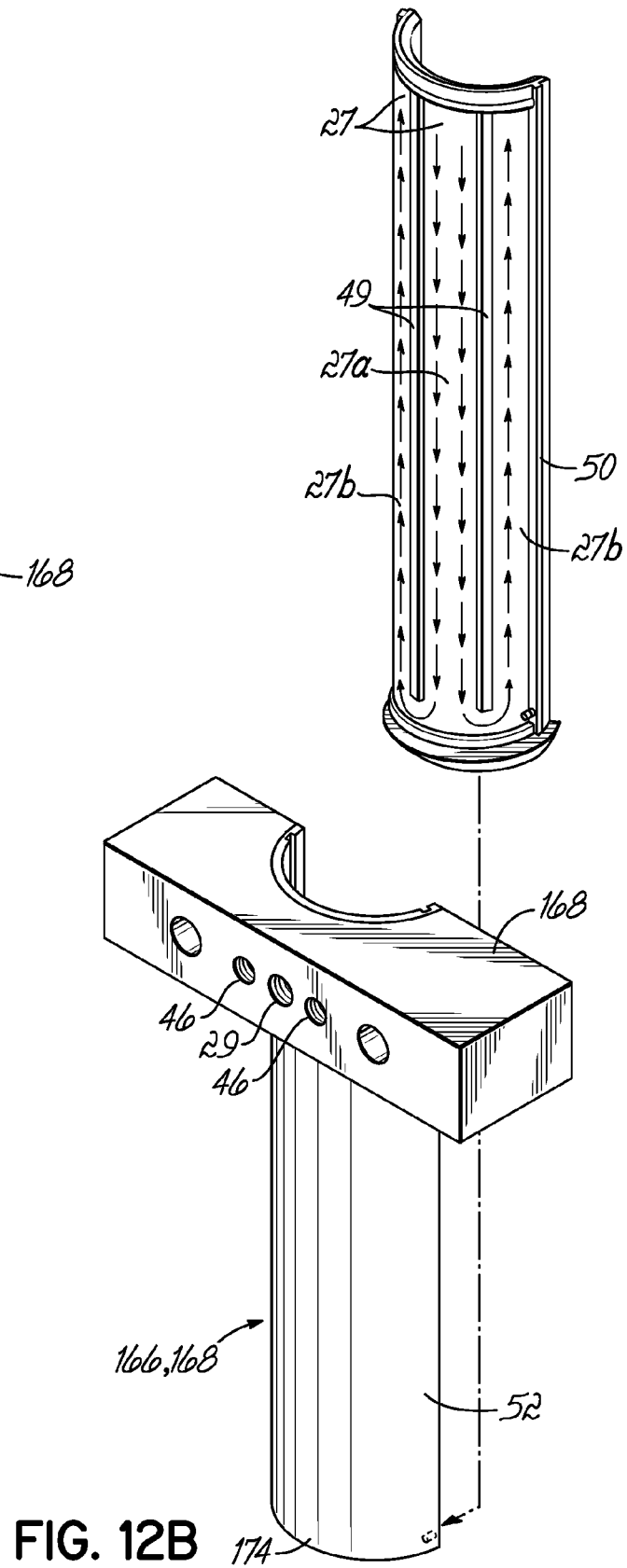
FIG. 12A
FIG. 12B

SURGICAL ACCESS SYSTEM AND METHOD OF USING THE SAME

FIELD OF THE INVENTION

The present invention generally relates to access systems useful in various surgical procedures, and more particularly to an improved access system useful for minimally invasive or open surgical procedures by providing methods of protecting the cellular structures at the surgical sites while providing a method of illuminating the same.

BACKGROUND OF THE INVENTION

In the past, certain surgical procedures required relatively large incisions to be made into the body in order to gain visual and instrumental access to a surgical site deep within the body. This incision provides a passageway by which various instruments operate upon the patient's anatomy. At times, it is necessary for the passageway to accommodate several instruments simultaneously, including but not limited to ancillary means for illuminating the surgical site or chilling the area to protect tissue and cellular integrity while still maintaining area for instruments performing the specific procedure.

By way of example, surgical procedures on posterior spine elements may have required relatively large incisions to be made to effectively operate on the spine elements. These large incisions are generally undesirable as they may result in increased damage to muscle tissue including, but not limited to, local denervation atrophy, a loss of support and stability creating pain, localized ischemia (the deprivation of oxygen), and potential scarring.

More recently, however, many surgical procedures are conducted using minimally invasive techniques that seek to minimize some of the undesirable aspects of past procedures. Such techniques typically involve splitting the muscle tissue, as opposed to cutting the muscle tissue, which in turn causes less damage to the muscle, increases the recovery times, and reduces patient discomfort.

Once a path to the surgical site is established, an access system, such as a surgical portal or retractor, may be inserted through the incision to provide the necessary retraction so as to establish an unencumbered path to the surgical site. Thus, the access port effectively defines a working bore or space and provides visual and instrument access to the surgical site in a minimally invasive manner. Additionally, studies have shown that localized hypothermia of the surgical site increases the survival rate of the cellular tissue by decreasing the tissue's need for nutrients and by inhibiting the ischemic cascade, with the longer-term effects of reducing the inflammatory response and cellular necrosis typically caused by the incision through the tissue and localized pressure on the tissue by the access system.

Although several minimally invasive access systems and techniques have been developed, there remains room for improvement. In particular, there is a need for an improved access system having an integrated ability to chill the surgical site to a hypothermic state to decrease the occurrence of cellular necrosis because of the increased pressure on tissue commonly found with the use of retractor systems in minimally invasive surgery. Additionally, there is a need for a method of illuminating a surgical site that addresses drawbacks of current systems and methods.

SUMMARY OF THE INVENTION

Aspects in accordance with the embodiments of the invention provide a method of thermally treating the tissue proximate to a surgical site during a surgical procedure. The method includes inserting a surgical access device into the patient. This surgical access device includes a body member having at least one conduit formed within the walls of the member. A chilled fluid is circulated through the at least one conduit so as to cool the tissue located proximate the body member. The chilled fluid may have a temperature in the range of approximately 10° C. and approximately 30° C. In one embodiment, the chilled fluid may have a temperature of approximately 25° C.

In another embodiment, the method provides for a chilled liquid, such as water, to be circulated through the at least one conduit. In another embodiment, the method provides for a chilled gas to be circulated through the at least one conduit. This chilled gas can be, for example, nitrogen or air.

The source of the chilled fluid may include a cold source. For example, in one embodiment, the chilled fluid may be supplied from a vortex tube where the cold gas stream from the vortex tube is drawn off and channeled into the at least one conduit. In yet another embodiment, the chilled fluid may be supplied from a heat exchanger, such as a refrigeration system, a chiller, or other suitable device capable of providing a chilled fluid stream.

The surgical access system may be formed as a portal having a singular body member or as a retractable access device having blade portions and/or one or more side plates. The at least one conduit may be formed within the walls of the portal body member, in one or more blade portions of the retractable access device, and/or in one or more side plates of the retractable access device.

These and other objects, advantages and features of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIGS. 12A and 12 B illustrate an enlarged cross-sectional view of a surgical access system in accordance with another embodiment of the invention;

DETAILED DESCRIPTION

Figure 1:
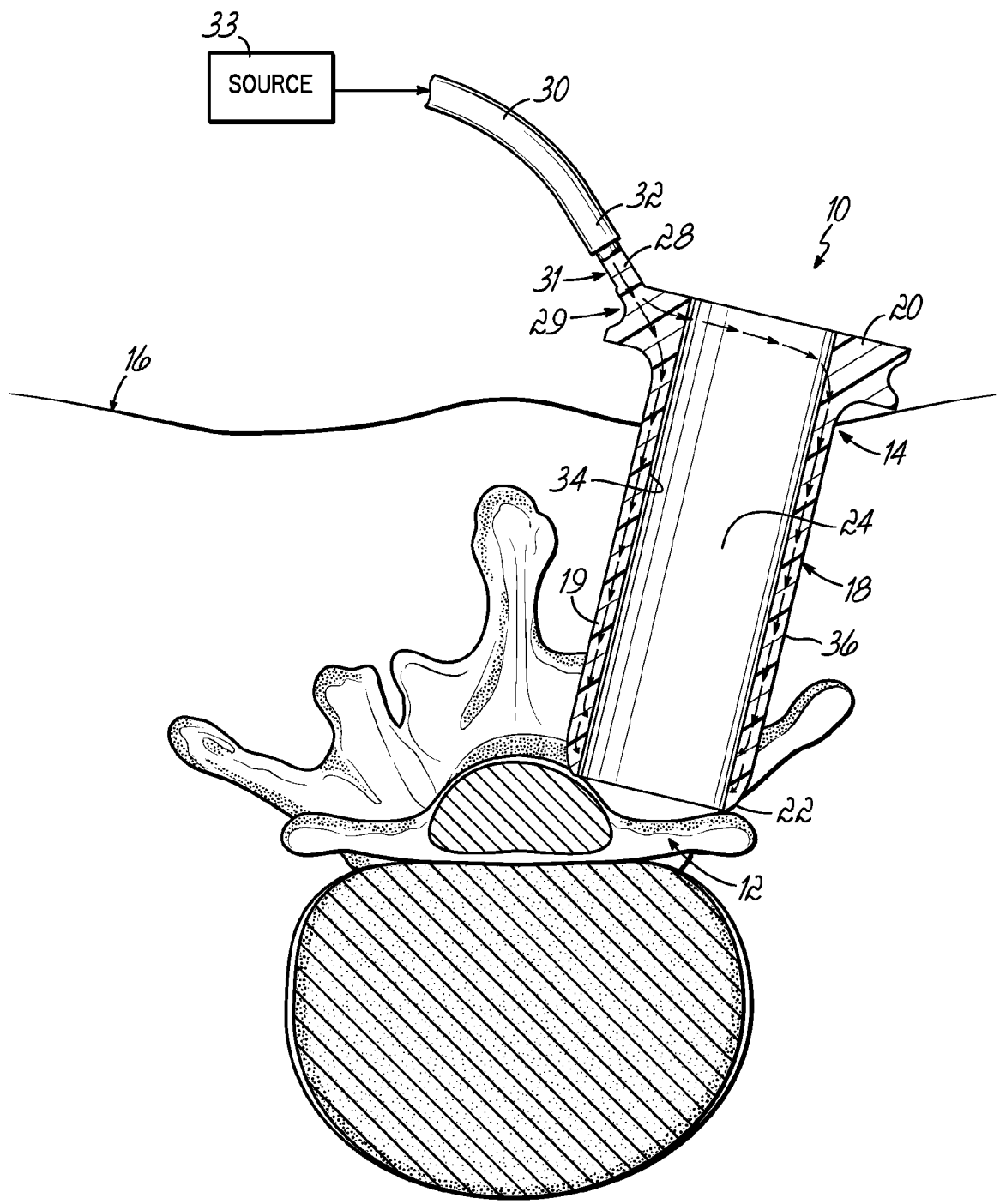
FIG. 1 is cross-sectional view of an access system in accordance with an embodiment of the invention used in posterior spine surgery.

Referring now to the figures, and to FIG. 1 in particular, a surgical access system includes a portal 10 that may be used during a surgical procedure to expose and provide visual and instrument access to a surgical site 12 that is spaced from an incision site 14 on a patient 16. In one exemplary embodiment, the portal 10 may be used for posterior spine surgery wherein certain spinal elements are located at the surgical site 12 and are spaced from an incision site 14 along the back of the patient 16. While the invention is shown and described in the context of posterior spinal surgery, the invention is not so limited as the portal 10 may be used in a wide variety of surgical procedures wherein the surgical site 12 is spaced from the incision site 14 and unencumbered access to the surgical site 12 via the incision site 14 is desired. Thus, the embodiment shown in FIG. 1 is only illustrative and those of ordinary skill in the art will recognize other surgical procedures that will benefit from aspects of the invention.

Figure 2:
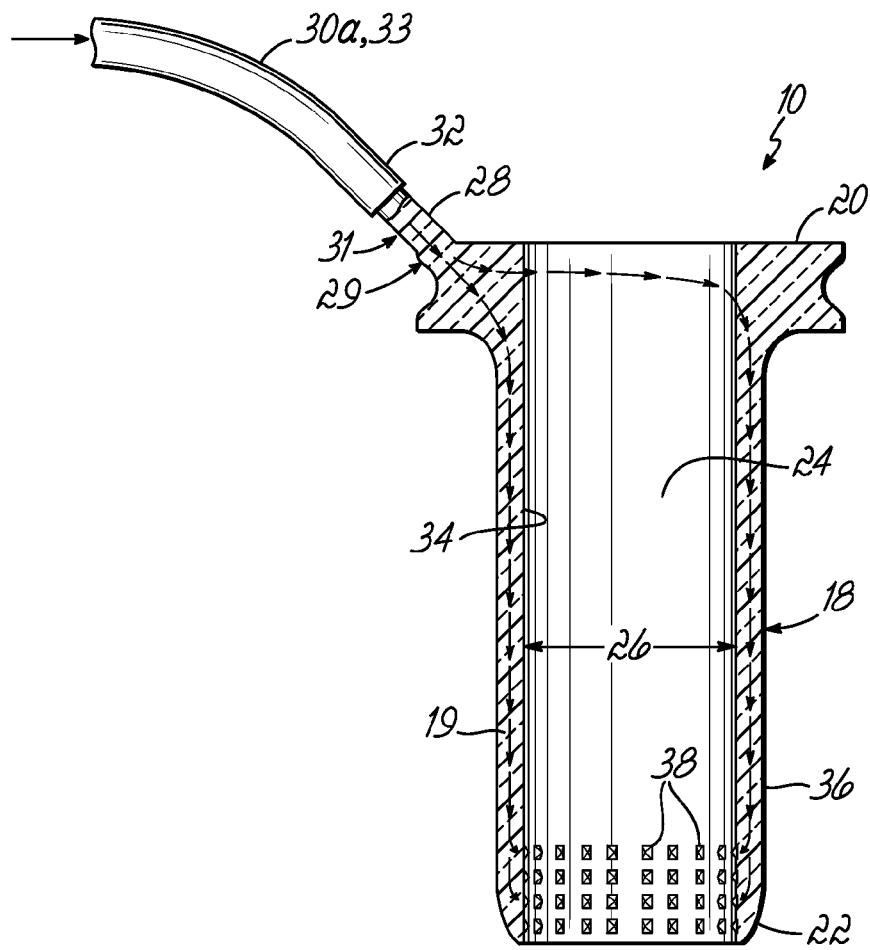
FIG. 2 is a cross-sectional view of a portal in accordance with an embodiment of the invention.

As shown in FIG. 1 the portal 10 generally includes a shaped body member 18, in one embodiment a tubular-shaped body member, having walls 19 extending from a proximal end portion 20 to a distal end portion 22 and a bore 24 extending between the proximal end portion 20 and distal end portion 22. The body member 18 may have a circular cross section with a bore diameter 26 (FIG. 2). Alternatively, the body member 18 may have other cross sections, such as oval, rectangular, triangular, etc, and is therefore not limited to a particular cross-sectional shape. As illustrated in FIG. 1, in use the distal end portion 22 of the portal 10 is adjacent the surgical site 12 within the body of the patient 16, and the proximal end portion 20 is adjacent the incision site 14 and outside the body of the patient 16. The bore 24 provides an access path for the insertion of various surgical instruments, implants, etc. therethrough so as to access the surgical site 12.

In some embodiments, the walls of the body member 18 may include integrally formed channels or conduits, which are traversed by fluids and/or energies emanating from a source 33. For example, in one embodiment, source 33 may provide a chilled fluid (e.g., liquid, gas, or flowable material) to the conduits to aid in preventing or reducing an ischemic or inflammatory response during or after surgical procedures. In another embodiment, source 33 may provide light to the conduits for illuminating the surgical site each of these embodiments will now be described in detail.

In regard to illumination of the surgical site, and as illustrated in FIG. 2, the material comprising the body member 18 may be of any optical grade material capable of transmitting light therethrough. For example, the material may be an optical grade thermoset or thermoplastic polymer. More particularly, the body member 18 may be formed from acrylic, polycarbonate, or other light transmitting materials as is known in the art. In this way, the body member 18 may operate as a "conduit" for transmitting light that illuminates the surgical site 12. To this end, the proximal end portion 20 of the portal 10 may include an external access port 29 to receive an adaptor 31 for coupling to source 33 (not shown). For example, in one embodiment, the adaptor 31 may be a male connector 28 that couples to source 33, which may be a light guide 30a (or more specifically a fiber optic light guide 30a), having a female connector 32 for coupling to the male connector 28. The male connector 28 is also formed from an optical grade material capable of transmitting light. For example, in one embodiment, the body member 18 may be formed through an injection molding process wherein the male connector 28 is integrally molded with the body member 18 and formed from the same optical grade material as the body member 18, although not so limited.

In operation, light from the light guide 30a acting as the source 33 enters the portal 10 via the male connector 28 and is transmitted from the proximal end portion 20 toward the distal end portion 22 of the body member 18 through the optical grade material. While some of the light may escape through the inner and outer surfaces 34, 36, respectively, of the body member 18, so as to perhaps give the portal 10 a slight glow, a significant portion of the light that enters the portal 10 is transmitted (via internal reflections, etc.) toward the distal end portion 22. In some embodiments, surfaces 34 and/or 36 may be masked in selected positions to limit or direct light. The distal end portion 22 of the portal 10 may then be configured to allow the light to emanate from the portal 10 so as to illuminate the surgical site 12. For example, the distal end portion 22 of the portal 10 may include a light-emitting region wherein light may escape the portal 10 so as to illuminate the surgical site 12. As described in more detail below, in one embodiment, the light-emitting distal end portion 22 may include a light directing portion such as surface features 38, that allow the light to escape from the body member 18. However, surface features 38 are but one such configuration of a light-emitting distal end portion 22 for portal 10. Other light-emitting structures or methods known to those of ordinary skill in the art may be used in the invention to allow light to escape the body member 18 so as to illuminate the surgical site 12.

Figure 3:
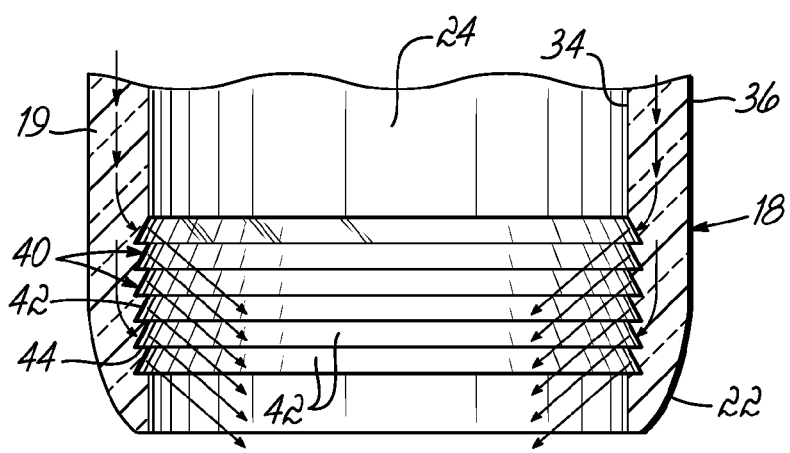
FIG. 3 is cross-sectional view of a distal end portion of a portal in accordance with an embodiment of the invention.

To this end, surface features 38, shown schematically in FIG. 2, may be formed on the inner surface 34 of the body member 18 adjacent the distal end portion 22. The features 38 allow light to essentially "escape" the portal 10 and illuminate the surgical site 12. In particular, the features 38 are generally non-planar with respect to the inner surface 34 so that light is no longer primarily internally reflected, but instead is reflected externally and out of the portal 10. As shown in FIG. 3, in one embodiment, the features 38 may be configured as one or more grooves or serrations 40 defining a plurality of angled surfaces 42, 44 configured to allow the light to escape the body member 18 and direct the light toward the surgical site 12. Those of ordinary skill in the art will appreciate a wide variety of surface features 38 in addition to grooves or serrations 40 that may be used to allow light to escape the body member 18 and direct the light toward the surgical site 12.

In one embodiment, the features 38 may be continuous around the inner surface 34 of the portal 10 (e.g., circumferential rings) as illustrated by the serrations 40 in FIG. 3. Alternatively, however, the features 38 may be discontinuous so as to define discrete circumferential sections in another example (not shown). In addition, those of ordinary skill in the art will recognize how to configure the features 38 so as to focus light at a specific location of the surgical site 12 and/or at a desired focal length. For instance, the angle of at least one of the angled surfaces 42, 44 relative to the inner surface 34 may be manipulated so as to direct light at a specific location and/or at a desired focal length. Moreover, in an exemplary embodiment, the features 38 may be integrally formed in the body member 18 through a molding process used in forming the body member 18. The invention, however, is not so limited as secondary processing steps may be used to form the features 38 in the body member 18.

Figure 4:
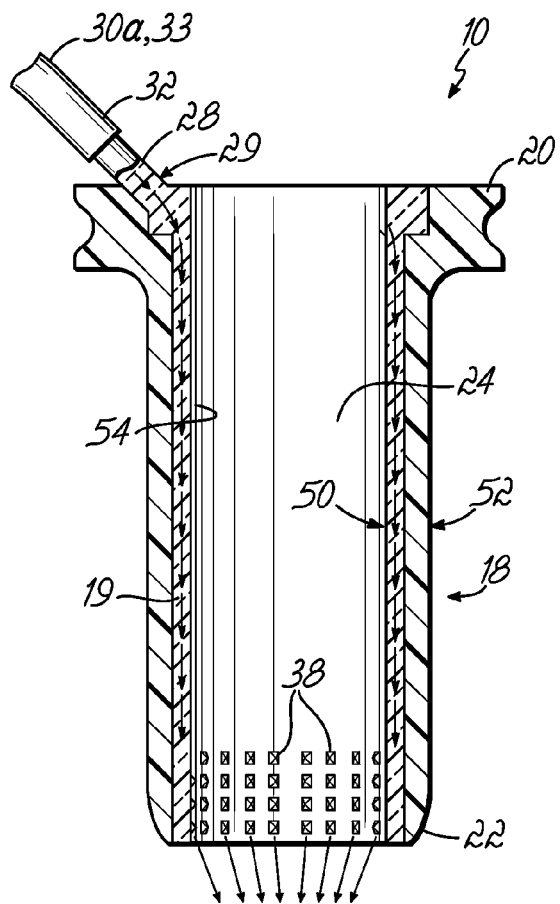
FIG. 4 is a cross-sectional view of a portal in accordance with another embodiment of the invention.

While a substantial portion of the entire body member 18 of the portal 10 described above may be formed from an optical grade material capable of transmitting the light toward the distal end portion 22 thereof, the invention is not so limited. For example, as shown in FIG. 4, in which like reference numerals refer to like features in FIGS. 1-3, a portal 10 may include a body member 18 having an inner shell 50 (FIG. 4) and an outer shell 52 (FIG. 4). The inner shell 50 may be formed from a first optical grade material capable of transmitting light therethrough, such as those previously identified above, and effectively operates as the conduit for transmitting the light to the surgical site. The outer shell 52, however, may be formed from a second material, which may or may not be an optical grade material and configured to enhance strength and stability of the body member 18, and thus the portal 10. For example, the outer shell 52 may be formed from nylon, acrylonitrile butadiene styrene (ABS), polyaryletherketone (PAEK), these materials with carbon fiber reinforcing, combinations of these materials, and/or other suitable materials.

Similar to that discussed above, the proximal end portion 20 of the inner shell 50 of the body member 18 includes an external access port 29 with an adaptor 31, such as male connector 28, that couples to a light guide 30a for supplying light to the portal 10, and thus to the surgical site 12 (not shown). As noted above, the male connector 28 may be integrally formed with the inner shell 50, as discussed in more detail below. In operation, light from a light guide 30a, acting as the source 33, enters the portal 10, and more particularly the inner shell 50, via the male connector 28 and is transmitted from the proximal end portion 20 toward the distal end portion 22 of the inner shell 50 through the optical grade material. The distal end portion 22 of the inner shell 50 may be configured as to allow the light to escape from the portal 10 and illuminate the surgical site 12 (FIG. 1). For example, surface features 38 may be formed on the inner surface 54 of the inner shell 50 adjacent the distal end portion 22.

In an exemplary embodiment, the portal 10 may at least in part be formed in a two-shot molding process wherein, for example, the inner shell 50 is molded in a first shot of the molding process by injecting the first optical grade material into a mold. The male connector 28 may be formed with the inner shell 50 during this first shot process. Subsequently, the outer shell 52 may be formed by injecting the second material into the mold during the second shot of the molding process so as to essentially overmold the first shell 50. Those of ordinary skill in the art will recognize that alternatively, the outer shell 52 may be formed during the first shot process, and the inner shell 50 (and external access port 29) formed during the second shot process. Those of ordinary skill in the art will further recognize other molding processes that may be used to produce the portal 10 with its inner and outer shells 50, 52. Portal 10 may also be formed through other processes known to those of ordinary skill in the art.

Figure 5:
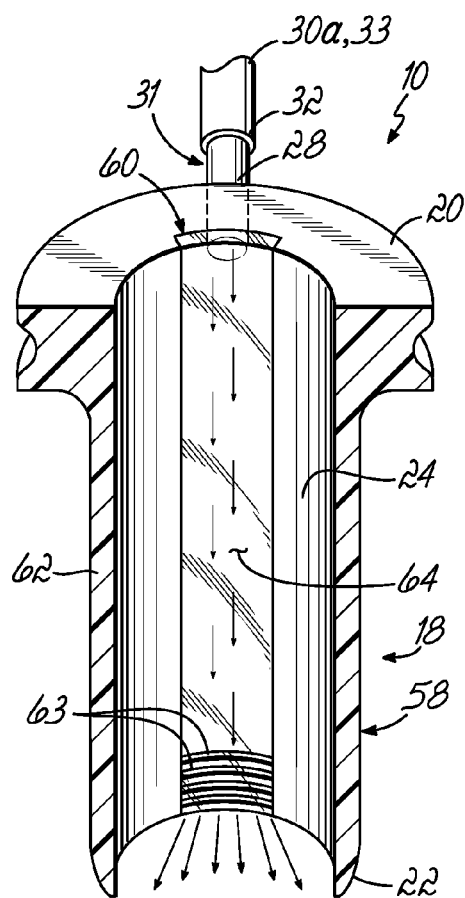
FIG. 5 is a cross-sectional view of a portal in accordance with another embodiment of the invention.

FIG. 5, in which like reference numerals refer to like features in FIGS. 1-3, shows another embodiment of a portal 10 constructed from multiple materials. In this embodiment, the portal 10 includes body member 18 having one or more strips 60 formed from a first optical grade material embedded in or forming a part of a shell 62 formed from a second material, which may or may not be an optical grade material. The first material, forming the strips 60, is capable of transmitting light from the proximal end portion 20 toward the distal end portion 22 of the body member 18 and includes those materials identified above for body member 18, such that the strips 60 effectively operate as the conduit for transmitting the light to the surgical site. The second material may be configured to enhance strength and stability of the portal 10 and includes those materials identified above for outer shell 52. In other words, in one embodiment, the strip 60 has a thickness that spans the thickness of the shell 62 (i.e., the strip 60 forms part of the shell 62). Alternatively, the strip 60 may have a thickness that is less than the thickness of the shell 62 so as to be embedded in the shell 62.

At the proximal end portion 20, the strip 60 includes an adaptor 31, such as male connector 28, that couples to a source 33, such as a light guide 30a acting as light source 33, for supplying light to the portal 10 and thus to the surgical site 12. The male connector 28 may be integrally formed with the strip 60, as discussed in more detail below. In operation, light from the light guide 30a enters the portal 10, and more particularly the strip 60, via the male connector 28 and is transmitted from the proximal end portion 20 toward the distal end portion 22 of the strip 60 through the optical grade material. At the distal end portion 22, the strip 60 may be configured to allow light to escape from the portal 10 so as to illuminate the surgical site 12. For example, a distal end portion 22 may include surface features 38, such as grooves 63, and may be formed on the inner surface 64 of the strip 60 adjacent the distal end portion 22.

Similar to that described above, the portal 10 may be formed in a two-shot molding process wherein, for example, the shell 62 is molded in a first shot of the molding process by injecting the second material into a mold. Subsequently, the strip 60 may be formed by injecting the first optical grade material into the mold during the second shot of the molding process. The male connector 28 may be integrally molded with the strip 60 during the second shot process. Those of ordinary skill in the art will recognize that alternatively, the strip 60 (and adaptor 31) may be formed during the first shot process, and the shell 62 formed during the second shot process. Those of ordinary skill in the art will further recognize other molding processes that may be used to produce the portal 10 with its strip 60 and shell 62. Portal 10 may also be formed through other processes known to those of ordinary skill in the art.

Figure 6:
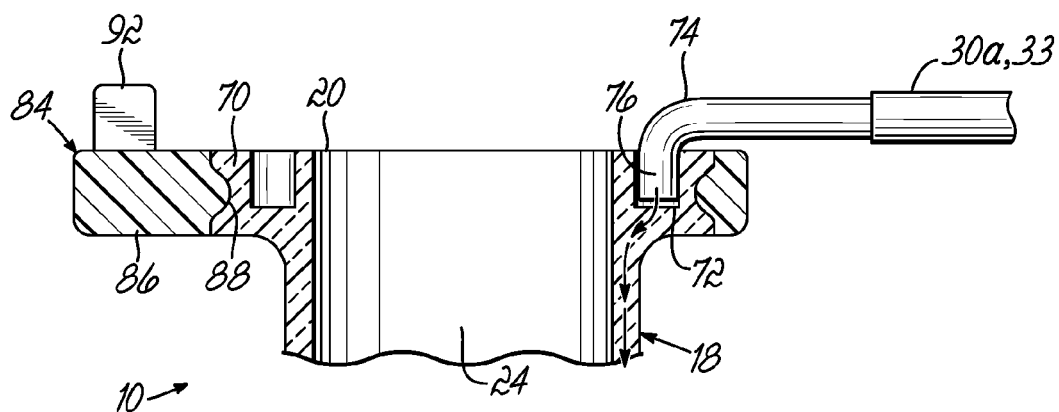
FIG. 6 illustrates a cross-section view of surgical access system in accordance with another embodiment.

In another embodiment, as shown in FIG. 6 and in which like reference numerals refer to like features in FIG. 2, the adaptor 31 for coupling to a source 33 of illumination energy may be configured as a female connector inserted upon the external access port 29, instead of the male connector 28 as illustrated in FIGS. 2-5. To this end, a portal 10 includes body member 18 having a proximal end portion 20 with a flange 70 extending outwardly therefrom. In this embodiment, the adaptor 31 on the portal 10 may be a female connector configured as, for example, a blind bore 72 formed in an upper surface of the flange 70. The blind bore 72 is configured to couple to a source 33, more specifically as related to this embodiment, a light guide 30a or other illumination means having a male connector 74. For example, the male connector 74 may include a rigid tube 76 that is received in blind bore 72, such as through an interference fit. To this end, the blind bore 72 and rigid tube 76 may be tapered such that the rigid tube 76 is secured to the portal 10 when positioned therein. Portal 10 operates in a manner consistent with the embodiments described herein, such that energy is transmitted between the source 33 and portal 10 via the blind bore 72 and is transmitted between the proximal end portion 20 and the distal end portion 22 of the body member 18 through the conduits and escapes the portal 10 via features 38 as described above, the conduits may be the body member 18 itself, an inner shell of the body member 18, or stripes formed in the body member 18. Thus, although not shown, the adaptor 31, such as blind bore 72, may also be used in the embodiments shown in FIGS. 2-5.

Figure 7:
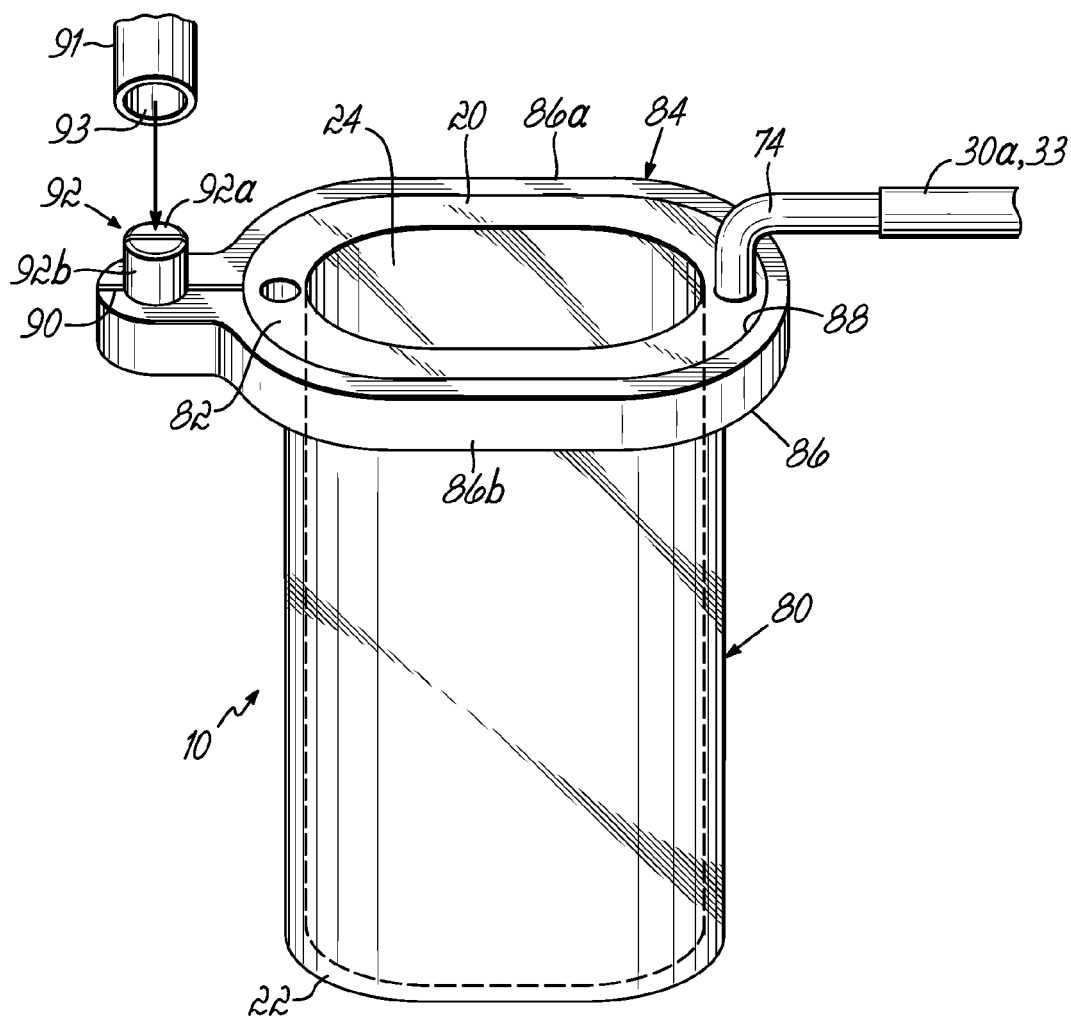
FIG. 7 illustrates a surgical access system in accordance with another embodiment of the invention.

Additional features may be used in combination with embodiments of the portal 10 as described above to facilitate the portal's 10 use during a surgical procedure. For example, as shown in FIG. 7, in which like reference numerals refer to like features in FIG. 2, a portal 10 includes a body member 18 having a proximal end portion 20 with a flange 70 extending outwardly therefrom. The body member 18 may be configured as any one of the embodiments described above. For example, a substantial portion of the entire body member 18 may be formed from a single material wherein the body member 18 operates as the conduit. Alternatively, the body member 18 may have an inner and outer shells, 50 and 52, respectively, configuration as illustrated in FIG. 4, or have a shell/strip 62/60 configuration as illustrated in FIG. 5. In any event, a clamping ring 84 may be removably coupled to the portal 10, and more particularly to the flange 70 of the body member 18 to facilitate use of portal 10.

The clamping ring 84 includes a body 86 having an opening 88 therein shaped and sized to correspond to the shape and size of the flange 70. In one embodiment, for example, the opening 88 is generally circular to match the circular cross-section of the flange 70, though not so limited. The clamping ring 84 has a split ring design with a first body section 86a and a second body section 86b coupled at one end thereof, but defining a gap 90 at the other end of the body sections 86a. The first and second body sections 86a, 86b operate as spring arms and define an open position and a closed position. In the open position, the clamping ring 84 may be snapped onto the flange 70 of the portal 10. Once positioned on the flange 70, the body sections 86a, 86b may be brought together, such as by squeezing, to close the gap 90 and secure the clamping ring 84 to the portal 10.

The clamping ring 84 is configured to couple to a mounting arm, shown schematically at 91 (e.g., a flexible arm), which is coupled to a support (e.g., operating table) and permits adjustment of the portal 10 in relation to the patient 16. To this end, the clamping ring 84 includes a connector for coupling to mounting arm 91. For example, the connector may be configured as a detent, such as post 92. As shown in FIG. 7, the post 92 may be configured to not only couple to mounting arm 91, but also to maintain the squeezing force on the clamping ring 84 so as to keep the clamping ring 84 secured to the portal 10. Thus, in one embodiment, the post 92 includes a first post portion 92a coupled to the first body section 86a, and a second post portion 92b coupled to the second body section 86b. When the body sections 86a, 86b are squeezed together, the first and second portions 92a, 92b form the post 92, which is received in a corresponding connector, such as a bore 93, of the mounting arm 91. The connection with the mounting arm 91 then maintains the coupling between the clamping ring 84 and the portal 10. Those of ordinary skill in the art will recognize that post 92 is an exemplary embodiment of a connector and the invention is not limited to such a configuration.

The clamping ring 84 is preferably made from a relatively rigid material, such as stainless steel, rigid polymeric material, or other suitable materials. The clamping ring 84 is configured to provide a more rigid and stable connection point for the mounting arm 91. In use, the ability to separate the portal 10 from the clamping ring 84 may allow the portal 10 to be used in a disposable manner while allowing the clamping ring 84 to be reused. Thus, for example, after a surgical procedure, the portal 10 may simply be discarded while the clamping ring 84 may be cleaned and sterilized and used in subsequent surgeries. Due to associated material costs for the clamping ring 84 relative to the portal 10, such use may result in an overall reduction in costs. The clamping ring 84 may further be configured to operate with a wide range of portal 10 configurations. For example, a set of portals 10 of different shapes, sizes, lengths, etc. may each have a flange 70 adjacent the proximal end portion 20 having a standard size so that each of the portals 10 may be secured within an opening 88 of one size in the clamping ring 84. A user may then choose an appropriate portal 10 depending on the specific application, desires of the user, etc., and use it with the clamping ring 84. Such interchangeability provides an access system with improved flexibility and robustness to accommodate a wide range of uses.

Figure 8:
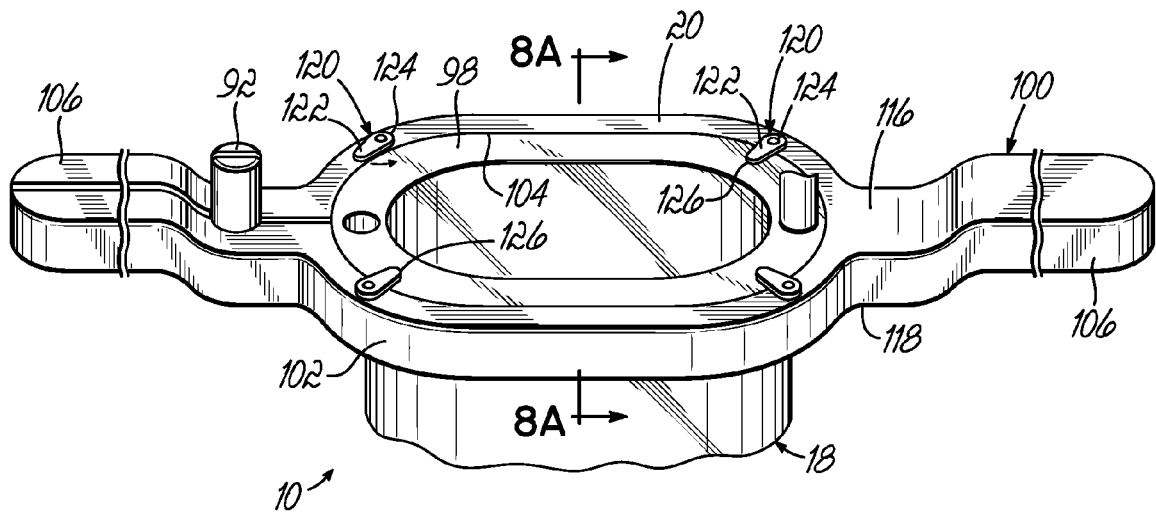
FIGS. 8 and 8A are perspective views of a portal in accordance with another embodiment of the invention.

In another embodiment, an access system may include a portal 10 used in combination with a handle apparatus 100 to facilitate the portal's 10 use during a surgical procedure. For example, as shown in FIG. 8, in which like reference numerals refer to like features in FIG. 2, a portal 10 includes a body member 18 having a proximal end portion 20 with a lip 98 extending outwardly therefrom. The body member 18 may be configured as any one of the embodiments described above. For example, substantially the entire body member 18 may be formed from a single material that operates as the conduits and as shown in FIG. 2. Alternatively, the body member 18 may have the inner/outer shell configuration as illustrated in FIG. 4 or have the shell/strip configuration as illustrated in FIG. 5. The portal 10 may be removably coupled to a handle apparatus 100, which facilitates use of the portal 10.

The handle apparatus 100 includes a body 102 having an opening 104 therein shaped and sized to correspond to the shape and size of the lip 98 at the proximal end portion 20 of the body member 18. In one embodiment, for example, the opening 104 is generally circular to match the circular cross-section of the lip 98, though not so limited. The handle apparatus 100 further includes at least one (two shown) outwardly projecting handles 106 adapted to be grasped by a doctor or other medical professional during use of the access system. The handle apparatus 100 may further include at least one connector, such as post 92 or other detent, for coupling the portal 10 to a mounting arm 91, similar to that discussed in FIG. 7 above.

Figure 8A:
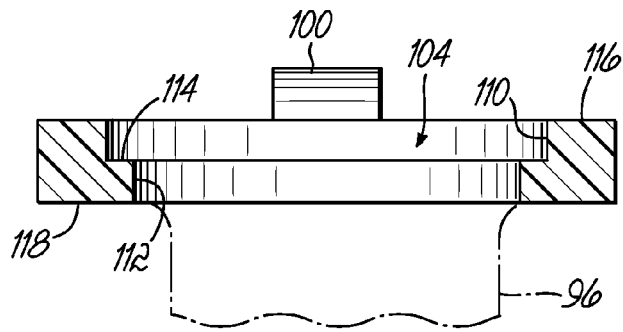

To couple the portal 10 to the handle apparatus 100, as in FIG. 8A, the opening 104 has a first portion 110 of a first cross dimension and a second portion 112 of a second cross dimension less than the first cross dimension to define a shoulder 114. The portal 10 is loaded into the handle apparatus 100 from the top by inserting the distal end portion 22 of the portal 10 through the opening 104 in a direction from a proximal surface 116 toward a distal surface 118 of the handle apparatus 100. The outwardly extending lip 98 of the portal 10 is closely received in the first portion 110 of the opening 104 and a lower surface of the lip 98 seats against the shoulder 114. Once the lip 98 is seated in the opening 104, the shoulder 114 prevents any further movement of the portal 10 relative to the handle apparatus 100 in a distal direction.

To prevent movement of the portal 10 relative to the handle apparatus 100 in a proximal direction, and thereby secure the portal 10 thereto, a latch mechanism 120 may be used. In one embodiment, the latch mechanism 120 may include an arm 122 having a first end 124 pivotally coupled to the proximal surface 116 of the handle apparatus 100, such as with a pin, and a second free end 126. The arm 122 is pivotable between an unlocked and locked position. In the unlocked position, the second end 126 overlies the proximal surface 116 so as to not project into the opening 104. In this way, the portal 10 may be inserted into the handle apparatus 100 without interference from the arm 122. Once the portal 10 is positioned in the opening 104, however, the arm 122 may be rotated to the locked position wherein the second end 126 overlies the lip 98 of the portal 10 and prevents proximal movement of the portal 10 relative to the handle apparatus 100. The arm 122 may be maintained in the closed position through an interference fit with the lip 98. Alternatively, the arm 122 may be spring biased toward the closed position (not shown).

Figure 9:
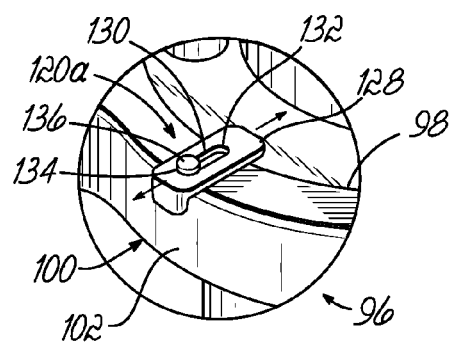
FIG. 9 is an enlarged cross-sectional view of a proximal end portion of a portal in accordance with an embodiment of the invention.

Those of ordinary skill in the art will recognize other latching mechanisms that may be used to secure the portal 10 within the opening 104. For example, as shown in FIG. 9, the latching mechanism 120a may include an arm 128 coupled to the proximal surface 116 of the handle apparatus 100 via a pin 136 received in a central slot 130 formed in arm 128. The arm 128 is slideable between an unlocked and locked position. In the unlocked position, the pin 136 is adjacent a first end 132 of the slot 130 so that the arm 128 does not project into the opening 104. In this way, the portal 10 may be inserted into the handle apparatus 100 without interference from the arm 128. Once the portal 10 is positioned in the opening 104, however, the arm 128 may be slid so that the pin 136 is adjacent a second end 134 and a portion of the arm 128 overlies the lip 98 of the portal 10 and prevents proximal movement of the portal 10 relative to the handle apparatus 100. The arm 128 may be maintained in the closed position through an interference fit with the lip 98. Alternatively, the arm 128 may be spring biased toward the closed position (not shown).

Similar to that described above, the handle apparatus 100 is preferably made from a relatively rigid material, such as stainless steel, rigid polymeric material, or other suitable materials. The handle apparatus 100 is configured to provide a gripping surface for manipulating the portal 10 and/or to provide a rigid and stable connection point for the mounting arm 91. In use, the ability to separate the portal 10 from the handle apparatus 100 may allow the portal 10 to be used in a disposable manner while allowing the handle apparatus 100 to be reused. Thus, for example, after a surgical procedure, the portal 10 may simply be discarded while the handle apparatus 100 may be cleaned and sterilized and used in subsequent surgeries. The handle apparatus 100 may further be configured to operate with a wide range of portal 10 configurations. For example, a set of portals 10 of different shapes, sizes, lengths, etc. may each have a lip 98 adjacent the proximal end portion 20 having a standard size so that each of the portals 10 may be secured within an opening 104 of one size in the handle apparatus 100. A user may then choose an appropriate portal 10 depending on the specific application, desires of the user, etc., and use it with the handle apparatus 100. Such interchangeability provides an access system with improved flexibility and robustness to accommodate a wide range of uses.

Portals 10 in accordance with the embodiments described above provide a number of advantages over existing portals 10. One advantage is that the body member 18 of the portal 10 itself is essentially the conduit for the light that illuminates the surgical site 12. In previous portals 10, a light tube or other light source would typically be inserted into the bore 24 of the portal 10 so as to illuminate the surgical site 12. Because space in the portal 10 is used for illumination purposes, less space is available for the passage of instruments, surgical implants, etc. Accordingly, larger portals 10 may then be required in certain surgical procedures. In various embodiments of the invention, however, the light source does not occupy space in the bore 24 of the portals 10. Instead, the light source is coupled to the external access port 29 to the bore 24 and the light is transmitted via channel through the body member 18 itself so as to illuminate the surgical site 12. Thus, space that would otherwise be occupied by the light source may now be used for instrument and/or implant access, and/or the overall size of the portal 10 may be reduced thereby improving the minimal invasive aspect of a surgical procedure.

Another advantage is that the body member 18 of the portals 10 described above may be formed from a material or materials that are radiolucent. For example, current portals 10 are typically formed from metal, such as titanium, or other materials that do not readily pass x-rays therethrough. Thus, under fluoroscopy or other imaging techniques, a doctor's view of various anatomic structures, such as spinal elements, may be blocked or obscured. In various embodiments of the invention, however, the materials selected for the portals 10, may allow x-rays to pass through the material such that the portal 10 does not effectively obscure a view of the surgical site 12 under fluoroscopy or other imaging techniques.

Figure 10:
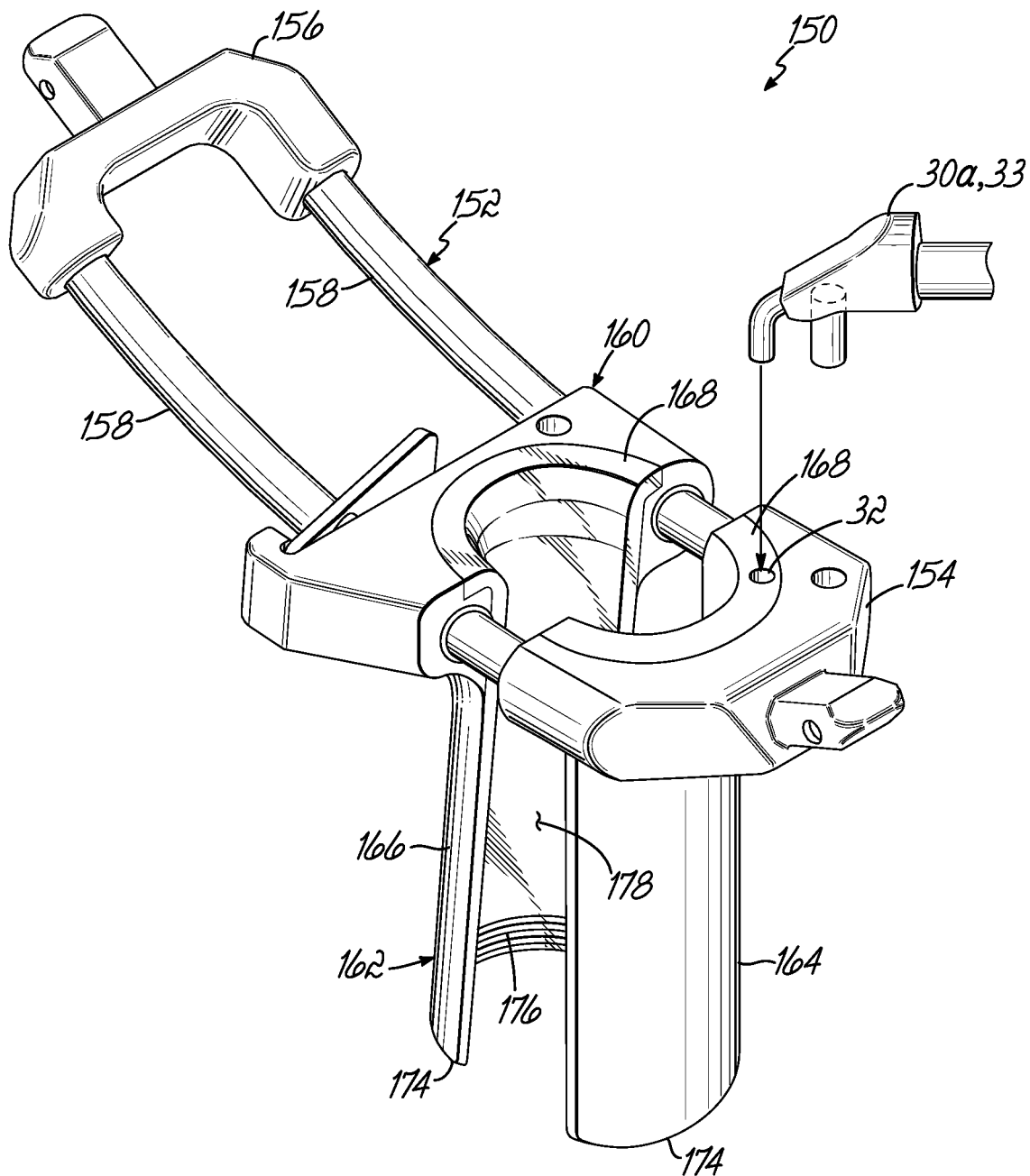
FIG. 10 illustrates a surgical access system in accordance with another embodiment of the invention.

The benefits gained by illumination of the surgical site described above are not limited to access systems configured as portals 10, but may apply to a broader range of access systems. For example, features of the invention may be readily incorporated in a surgical retractor to provide similar benefits. By way of example and without limitation, retractors as described in U.S. patent application Ser. Nos. 11/458,662; 11/619,214; and 11/623,937, the disclosures of which are incorporated by reference herein in their entirety, may benefit from inventive features as described above. Other retractors that may benefit from the illumination and chilling systems of this application include those described in U.S. Pat. No. 7,226,451, the disclosure of which is incorporated by reference herein in its entirety. To this end, FIG. 10 illustrates an exemplary retractor 150 including a frame 152 having a first base portion, such as member 154, a cross member 156 opposite the base member 154, and a pair of rails 158 extending from the base member 154. The retractor 150 further includes a second portion, such as slide 160, mounted on the rails 158 and movable therealong relative to the base member 154. A bore 24 between the incision site 14 and the surgical site 12 (FIG. 1) is provided by a segmented body member 162 having a first blade portion 164 and a second blade portion 166. The first blade portion 164 may be coupled to the base member 154 and the second blade portion 166 may be coupled to the slide 160 and moves therewith. Movement of the slide 160 and second blade portion 166 effectively increases the size of the bore 24 to the surgical site 12. This increase in the bore 24 size is achieved by splitting and stretching the muscle as opposed to cutting, which provides certain advantages, as more fully discussed in the patent applications identified above.

In one embodiment, at least one of the first or second blade portions 164, 166 may be formed from an optical grade material acting as conduits capable of transmitting light therethrough. The material may be, for example, an optical grade thermoset or thermoplastic polymer. More particularly, at least one of the first or second blade portions 164, 166 may be formed from acrylic, polycarbonate, or other light transmitting materials as is known in the art. In this way, at least one of the first or second blade portions 164, 166 may operate as a conduit transmitting light that illuminates the surgical site 12.

To this end, the proximal end portion 168 of the selected blade portion(s) 164, 166 for transmitting light may include an adaptor 31, such as a female connector 32, that couples to a light guide 30a acting as the source 33, such as fiber optic light guide 30a. Alternatively, the adaptor 31 may also be a male connector 28, such as male connector 28 shown in FIG.

2. In this case, the male connector 28 may also be formed from an optical grade material capable of transmitting light and may be integrally formed with the selected blade portion(s) 164, 166. The male connector 28 may extend through at least a portion of the bodies of the base member 154 or slide 160 so as to be accessible from a proximal surface 116 thereof, thereby facilitating coupling to the light guide 30a. In addition, similar to that described above, the selected blade portion(s) 164, 166 that are to be coupled to the light guide 30a and transmit light therethrough may have a distal end portion 174 configured to allow the light to escape from the selected blade portion(s) 164, 166 so as to illuminate the surgical site 12. In some embodiments, blade portions 164, 166 may be masked in selected portions to limit or direct light. The distal end portion 174 may include a light-emitting region. For example, surface features 38, such as grooves 63 or serrations 40 as previously described, may be formed on the inner surface 178 of the selected blade portion(s) 164, 166 adjacent their distal end portion 174.

In operation, light energy from the light guide 30a enters the selected blade portion(s), i.e., first blade portion 164, second blade portion 166, or both, via the female connector 32. The light is transmitted from the proximal end portion 168 toward the distal end portion 174 of the retractor 150 through the optical grade material and escapes the selected blade portion(s) 164, 166 from the features 176 formed thereon so as to illuminate the surgical site 12.

Those of ordinary skill in the art will recognize that certain of the alternate embodiments described in reference to the portals 10 in FIGS. 2-5 may also apply to the retractor 150 shown in FIG. 10. Thus, in an alternate embodiment, the features 176 may be continuous or discontinuous along the selected blade portion(s) 164, 166. In another alternate embodiment, a male connector 28 may be used in lieu of the female connector 32, as noted above.

In addition to these alternate embodiments, the selected blade portion(s) 164, 166 may be formed from multiple materials similar to that described in FIGS. 4 and 5. Thus, for example, in one alternate embodiment similar to FIG. 4, the selected blade portion(s) 164, 166 may have an inner shell and outer shell configuration, wherein the inner shell is formed from the optical grade material capable of transmitting light and the outer shell is formed from a structural material configured to add strength and stability to the selected blade portion(s). In another alternate embodiment similar to FIG. 5, the selected blade portion(s) 164, 166 may include a shell formed from a structural material configured to provide strength and stability to the blade portion(s) and at least one strip formed from an optical grade material capable of transmitting light. Furthermore, the blade portions 164, 166 may be removably coupled to the base member 154 and/or slide 160, respectively, so that the blade portions may be used in a disposable manner while the frame 152 and remaining portions of the retractor 150 may be reused. The ability to separate the blade portions 164, 166 from the frame 152 provides the advantages described above.

Figure 11:
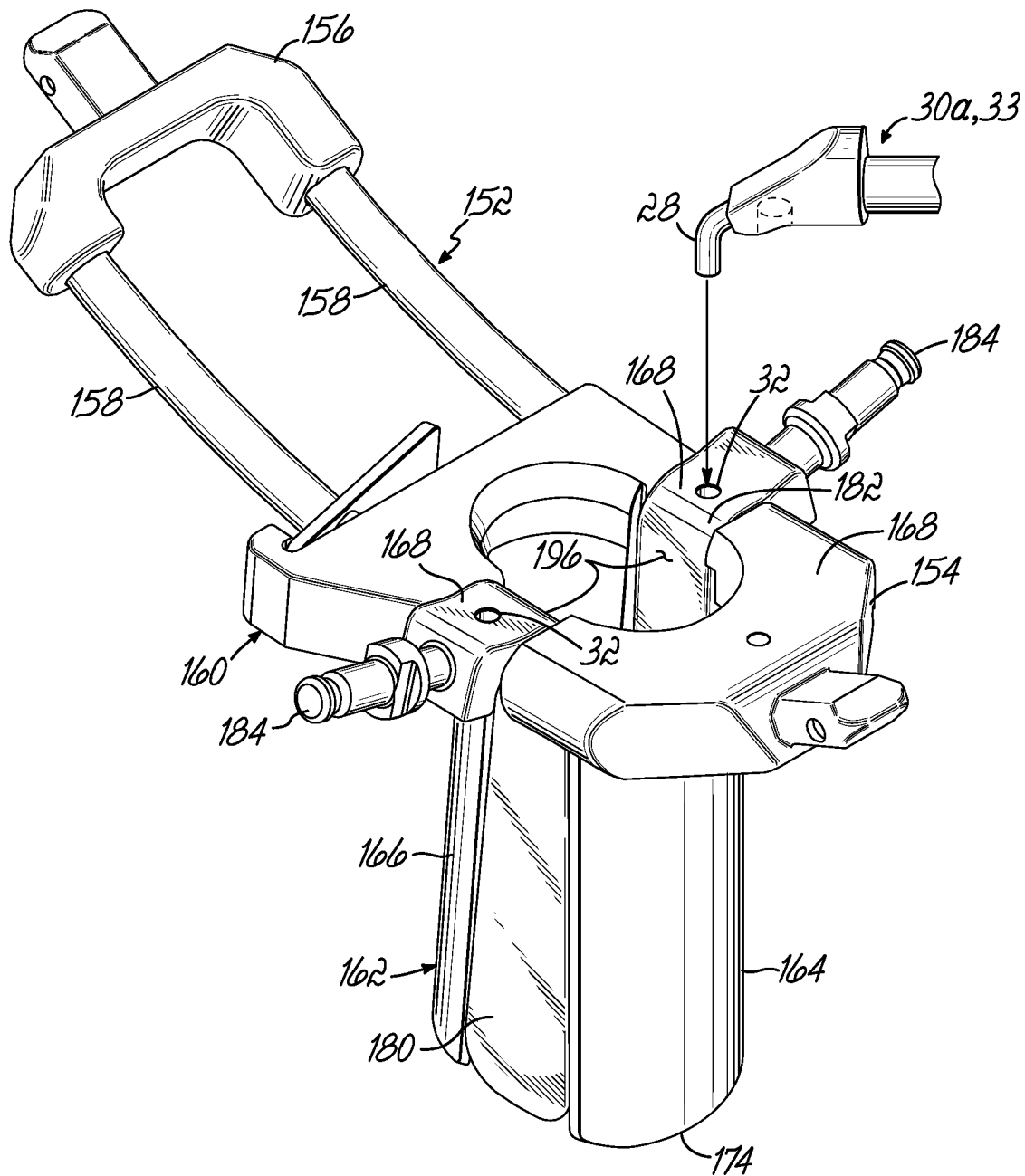
FIG. 11 illustrates a surgical access system in accordance with another embodiment of the invention.

As discussed in U.S. patent application Ser. Nos. 11/458,662; 11/619,214; and 11/623,937, as the slide 160 is separated from the base member 154, second blade portion 166 is moved away from first blade portion 164 to expand the bore 24. Consequently, a gap 90 forms between the side edges of the blade portions 164 and 166 that may allow surrounding tissue to enter the access path and possibly occlude instrument access therethrough. As shown in FIG. 11, in which like reference numerals refer to like features in FIG. 10, to prevent or reduce such encroachment of the surrounding tissue when the blade portions 164, 166 are separated, the retractor 150 may include one or more (two shown) side plates 180, 182 adapted to be mounted on rails 158 via an attachment member, such as a set screw 184.

In another embodiment, instead of, or in addition to at least one of the blade portions 164, 166 transmitting light to illuminate the surgical site 12, at least one of the side plates 180, 182 may be configured to transmit light therethrough so as to illuminate the surgical site 12. To this end, at least one of the side plates 180, 182 may be formed from an optical grade material capable of transmitting light. The material may be, for example, an optical grade thermoset or thermoplastic polymer. More particularly, at least one of the side plates 180, 182 may be formed from acrylic, polycarbonate, or other light transmitting materials as is known in the art. In this way, at least one of the plates 180, 182 may be used to transmit light so as to illuminate the surgical site 12.

Similar to previous embodiments, the proximal end portion 186 of at least one of the side plates 180, 182 may include an external access port 29 with an adaptor 31, such as a female connector 32 that couples to a source 33 of fluid or light. The connector may also be a male connector 28, such as male connector 28 shown in FIG. 2. In this case, the male connector 28 is also formed from a material capable of transmitting light and may be integrally formed with the selected side plate(s) 180, 182, such as through a molding process or material selection. In addition, similar to that described above, the selected side plate(s) 180, 182 that are to be coupled to the source 33 and transmit light therethrough may have a distal end portion 174 configured to allow the fluid or light to escape from the side plate(s) and into the surgical site 12. For example, surface features 38, such as grooves 63 or serrations 40 as previously discussed, may be formed on the inner surface 196 of the selected side plate(s) 180, 182 adjacent their distal end portion 22.

In operation, light from the light guide 30a enters the selected side plate(s), i.e. side plate 180, side plate 182, or both, via the male connector 28. The light is transmitted from the proximal end portion 186 toward the distal end portion 192 through the optical grade material and escapes the selected side plate(s) 180, 182 from the features formed thereon so as to illuminate the surgical site 12.

Those of ordinary skill in the art will recognize that certain of the alternate embodiments described in reference to the portals 10 and/or blade portions 164 also apply to the side plate(s) 180, 182. Thus, in an alternate embodiment, the exits at the distal end portion 174 may be continuous or discontinuous along the side plate(s) 180, 182. In another alternate embodiment, a male connector 28 may be used in lieu of the female connector 32, as noted above. Additionally, the selected side plate(s) 180, 182 may be formed from multiple materials similar to that described in FIGS. 4 and 5. Thus, for example, in one alternate embodiment similar to FIG. 4, the selected side plate(s) 180, 182 may have an inner shell 50 and outer shell configuration 52, wherein the inner shell 50 is formed from a material capable of transmitting fluid, light, or energy and the outer shell 52 is formed from a structural material configured to add strength and stability to the selected side plate(s) 180. In another alternate embodiment similar to FIG. 5, the selected side plate(s) 180, 182 may include a shell 62 formed from a structural material configured to provide strength and stability to the side plate(s), 180 and 182, and at least one strip 60 formed from a material capable of transmitting light.

The embodiments described above were directed to illumination of the surgical site by channeling light energy through the "conduits" in the body of the portal, blade, and/or side plate. As noted above, however, in another aspect in accordance with the invention, a chilled fluid may be channeled through at least one conduit in the various bodies to protect tissue and cellular viability.

In this regard, and as illustrated in FIG. 12, the at least one conduit 27 may be formed between the inner shell 50 and the outer shell 52 of the selected blade portion(s) 164, 166. The at least one conduit may be constructed in a fluid-tight fashion as to direct the transmission of a chilled fluid (e.g. water, air, etc) through the selected blade portion(s) 164, 166. The material of the blade portion(s) 164, 166 may be formed of a polymer or other suitable materials that are compatible with surgical procedures and nonreactive with the fluids being transmitted. In this way, the at least one conduit in the selected blade portion(s) 164, 166 operates for the transmission of a chilled fluid from the source 33, (i.e., a vortex tube, heat exchanger, or heat sink) through the at least one conduit in the selected blade portions so as to cool tissue proximate to the selected blade portions. A vortex tube is available from ITW Air Management Vortec Products located in Cincinnati, Ohio.

To this end, the proximal end portion 174 of the selected blade portion(s) 166, 168 includes an external access port 29 attachable to an adaptor 31 (not shown) for coupling to the source 33. As described previously, the adaptor 31 may be a male connector 28 that couples to the source 33 having a female connector 32. Whereas in another embodiment, the adaptor 31 may be female connector 32 attaching the source 33 having a male connector 28. Other means of interconnectivity would be known within the art and up to the discretion of the surgeon's needs.

The at least one conduit 27 may be constructed within the selected blade portion(s) 164, 166 such that chilled fluid will lower the temperature of the tissue immediately adjacent or proximate to the retractor 150 as it extends from the incision site 14 toward the surgical site 12 (see FIG. 1), thus decreasing the occurrence of ischemia, necrosis, or inflammation due to the increased pressure, stress, etc. caused by the retraction. This decreased occurrence of necrosis provides the benefit of a faster rate of recovery from the invasive surgery. In an exemplary embodiment, the at least one conduit 27, provides multiple fluid pathways extending from the proximal end portion 168 toward the distal end portion 174. As illustrated in FIG. 12B, linear conduits 27a, b extending longitudinally along the length of the selected blade portion(s) 164, 166 are separated by ribs 49. However, other configurations may be known and used according to viscosity and needs of the fluid being transmitted therethrough. For example, as illustrated in FIG. 12B, the inner shell 50 and outer shell 52 couple together in a manner such that the ribs 49 sealingly engage the inner wall of the outer shell 52 and may form fluid-tight conduits 27a, b.

In operation, a fluid enters source 33 and is chilled to between approximately 10° C. to approximately 30° C., and preferably to approximately 25° C., and wherein normal core body temperature is 37° C. It should be noted that any fluid compatible with the surgical process might be used, including but not limited to water or non-reactive gases, such as air or nitrogen. The chilled fluid now enters the at least one conduit of the selected blade portion(s) 164, 166 via the adaptor 31 of the external access port 29 according to one of the manner described above. The chilled fluid is transmitted from the proximal end portion 20 toward the distal end portion 22 of the body member 18 by ingress conduit(s) 27a and returns again to the proximal end portion 20 by egress conduit(s) 27b. Along this pathway, the natural process of thermal exchange occurs, i.e. tissue adjacent the incision site 14 and surgical site 12 release heat energy (are cooled) to the chilled fluid (which is warmed within the conduits 27a, b). The continuous flow of chilled fluid into the ingress conduit(s) 27a and through the egress conduit(s) 27b assures the continued thermal exchange. Egress conduit(s) 27b are in fluid communication to an exhaust 46 for removing the now warmed fluid. In this way, and as illustrated in FIG. 12A, both the external access port 29 for supplying the chilled fluid and the exhaust 46 may be located at the proximal end portion 168 of the selected blade portion(s) 164, 166.

It would be known in the art the manner by which to adapt the present invention such that the fluid is recycled within a closed loop system comprised on the selected blade portion (s) 164, 166, the source 33, and related fluid connectors such that a constant supply of fresh fluid is not required. Alternatively, the system would remain open such that a constant flow of new fluid is constantly supplied from the heat sink while the warmed fluid exiting the exhaust 46 is disposed in a proper fashion.

Accordingly, the chilled fluid entering at the external access port 29 should be less than 37° C., that is, the average normal core body temperature; however, the temperature would preferably be between approximately 10° C. and approximately 30° C., as this temperature range is most efficient at reducing inflammation, ischemia, and/or necrosis without causing the adverse affects of hypothermia-related cellular death.

While not specifically illustrated and described herein, one skilled in the art would appreciate that chilling of the surgical site 12 may also be accomplished using a portal 10 similar to those shown in FIGS. 1-11 and wherein the at least one conduit is constructed within the body member 18 of the portal 10. Operation of a chilled portal in similar to that described above and thus will not be discussed in detail.

Formation of the selected blade portion(s) 164, 166 may be by a two-shot molding process, wherein an inner shell 50 is molded in a first shot of the molding process by injecting a material into a mold. Subsequently, the outer shell 52 may be formed by injecting the same, or a different, material into the molding during the second shot of the molding process so as to essentially overmold the inner shell 50 containing the at least one conduit. Those of ordinary skill in the art will recognize that alternatively, the outer shell 52 may be formed during the first shot process, and the inner shell 50 formed during the second shot process. Those of ordinary skill in the art will further recognize other molding processes that maybe used to produce the inner and outer shells 50, 52 having at least one conduit formed therein.

During the surgical procedure making use of a retractor 150 according to one embodiment of the present invention, the surgeon creates an incision at the incision site 14 using a scalpel in a known manner. The blade portions 164, 166 of retractor 150 are inserted through the incision site 14 toward the surgical site 12. The second blade portion 166 moves along the slide 160 to increase the size of the bore 24 and such that the surgical site 12 becomes accessible. In one embodiment, the surgeon may initiate the flux of the chilled fluid through the blade portions 166, 168 prior to inserting the retractor 150 into the incision site 14. In another embodiment, the surgeon may decidedly wait until after inserting and expanding the blade portions 166, 168 of the retractor 150 to initiate the flux of chilled fluid. Other nuances related to the use of chilled retractor 150 will be known within the art or explicitly included herein, with respect to the description of particular embodiments.

The at least one conduits may provide a single flow path from the external access port 29 to the exhaust 46, by which one ingress channel 27a progressively converts to one egress channel 27b. Alternatively, it would be possible to include several small ingress conduits 27a converging to a single large egress channel 27b. Other arrangements, or even interconnections, between the conduits 27 would be known in the art and are adaptable to the particular needs of the surgical procedure and the level of chilling required.

In another embodiment, a vortex tube acting as the source 33 would provide cooled gas as the chilled fluid to the selected blade portion(s) 164, 166. As such, the at least one conduit would be constructed as described previously, but also in a manner such as to contain the pressures and flux created by the flow of gas.

A vortex tube is a device that separates a compressed gas into cold and hot streams without the use of mechanical parts. Pressurized air is readily available within the hospital setting, thus the vortex tube provides one easily implementable embodiment for chilling the blade structure 150. Pressurized gas systems, both air and nitrogen, which are typically available within a hospital operating room having pressure ranges from 100-150 psi are also appropriate for use with a vortex tube. For example, a commercially available vortex tube requires a minimum operational pressure of approximately 80 psi, which is easily attainable with the hospital systems. As such, the utilization of a vortex tube to generate a stream of chilled gas from the pressurized sources within the traditional operating room would adequately chill the selected blade portion(s) 164, 166 in accord to this embodiment. In operation, these pressurized air systems would connect to the input of an appropriate vortex tube while the cold stream output of the vortex tube connects to the selected blade portion(s) 164, 166 via an adaptor 31 and discussed in detail above. That is, the outlet of the vortex tube could include a connector adaptable to adjoin the adaptor 31 of the external access port 29 of the selected blade portion(s) 164, 166 for an efficient transfer of the chilled gas from the vortex tube and into the now chilled selected blade portion(s) 164, 166. Use of a vortex tube is particularly useful as a virtually maintenance free system. That is, a vortex tube as the source 33 is a one-time expense not requiring additional costs or routine-quality control. However, alternative embodiments are envisioned for those circumstances wherein a supply of pressurized gas is not readily available or not an option. For example, a heat exchanger, chiller, or other device capable of providing a chilled fluid stream may be used. These devices may use Freon or other refrigerants, a supply of water or saline, or other fluids may be used to chill the retractor blades in a manner described herein.

Figure 13:
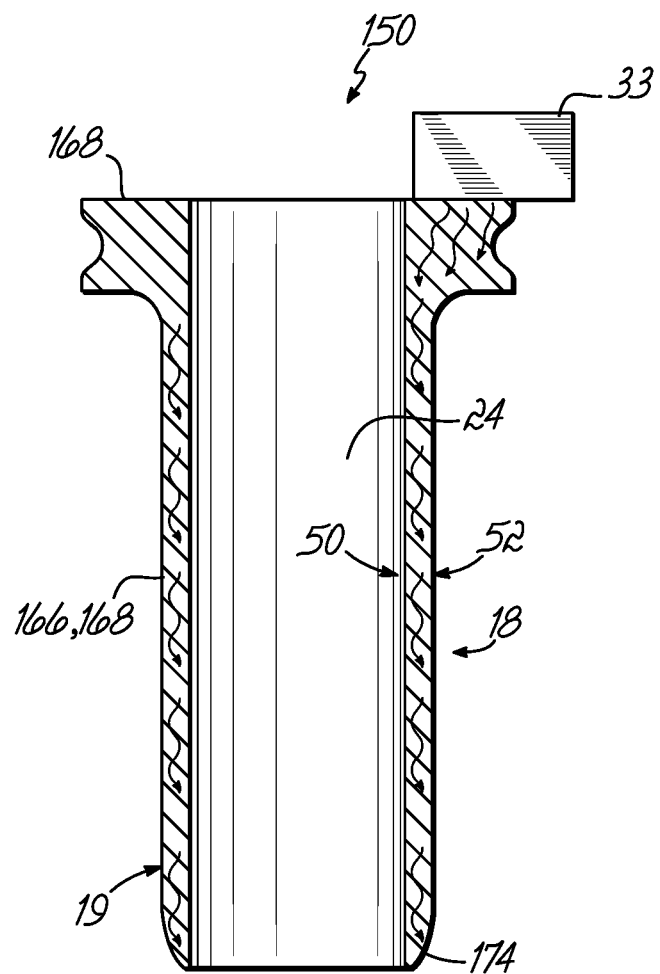
FIG. 13 is a cross-sectional view of a surgical access system in accordance with another embodiment of the invention.

In yet another aspect and as shown in FIG. 13, the walls 19 of the blade structure 150 may be constructed from a material that permits the transfer of heat energy from the distal end portion 174 toward the proximal end portion 168 and eventually to a cooled body acting as the source 33. Much as discussed previously with respect to FIG. 2, the selected blade portion(s) 164, 166 may be constructed of a material based on its thermally conductive properties. For example, titanium or aluminum, which provide quick and adequate thermal transfer may be used to form the walls 19 of the selected blade portion(s) 164, 166. The source 33, a chilled body acting as a heat sink, is positioned in thermal communication with the proximal end portion 168 of the selected blade portion(s) 164, 166. In operation, the naturally occurring thermal exchange would direct heat from the tissue located proximate the surgical and incision sites 12 and 14, along the walls 19 from the distal end portion 174 toward proximal end portion 168 and ultimately to the cooled body acting as the source 33. The heat transferred to the heat sink may then be dissipated to a larger heat sink such that the temperature of the chilled body atop the proximal end portion 168 remains at a low temperature, which is between approximately 10° C. and approximately 30° C., and preferably at approximately 25° C.

The advantage of these chilled retractor 150 embodiments, is the ability to locally chill the tissue proximate the incision site 14 and surgical site 12 as to reduce the occurrence of inflammation, cell necrosis, cell atrophy, cell ischemia, and to decrease pain and recovery time. These are particularly useful in that the localized chilling does not require the insertion of a separate medical instrument into the bore 24 (for all the reasons discussed previously with respect to illumination). Additionally, the present embodiments as described above are all incorporated into the walls 19 of the access system.

In yet another embodiment and as described in detail above with respect to illumination, the side plates 180, 182 may be formed of a thermally conductive material, such as aluminum or titanium, for the transmission of heat energy. To this end, a heat sink is placed in thermal contact with the proximal end portion 168 of retractor 150 in a way such that heat is extracted from the tissue proximate the surgical site 12 and incision site 14, passes along the thermally conductive side plates 180 to the proximal end portion 168 of retractor 150, and inevitably to the heat sink located thereat.

Figure 14:
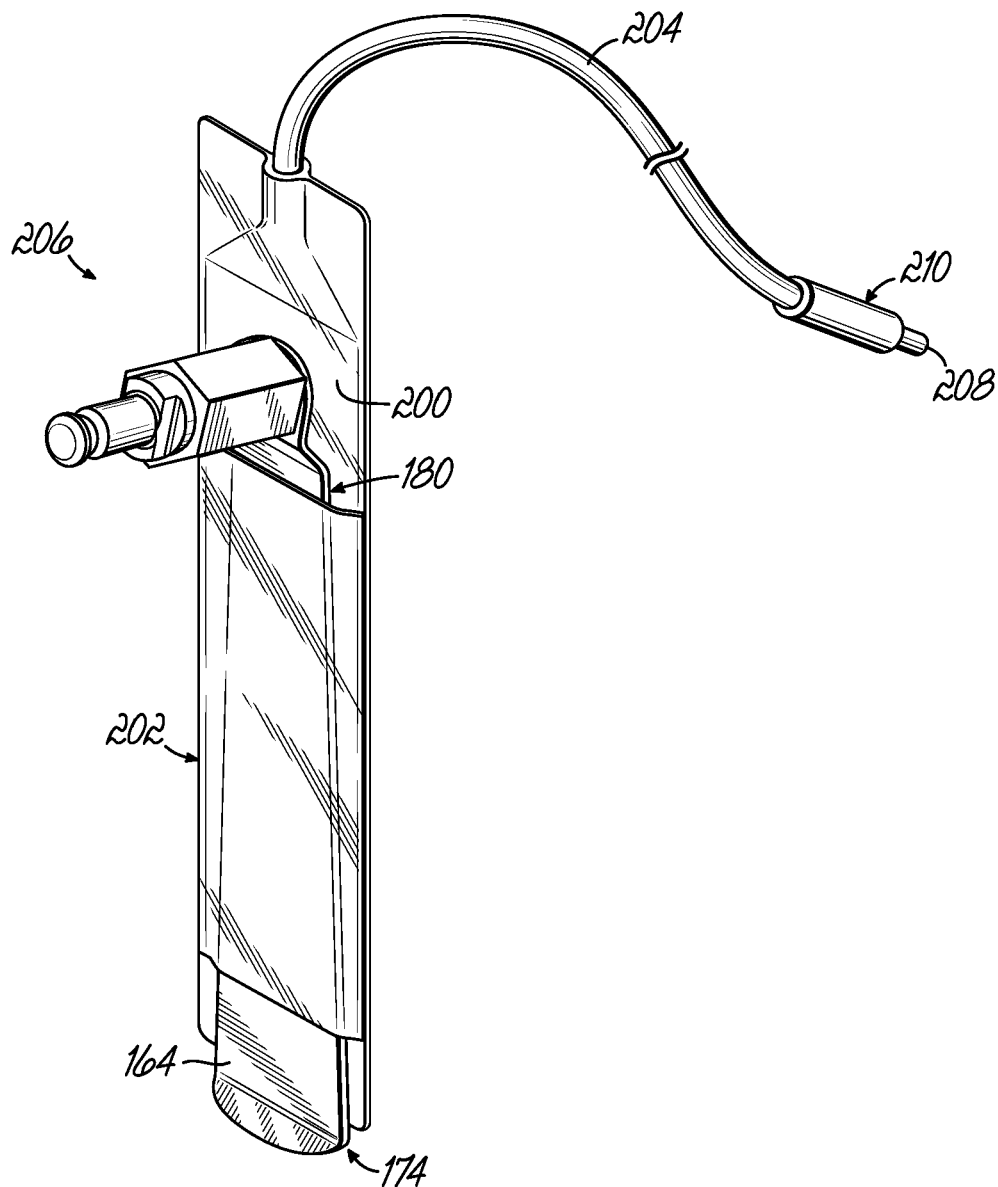
FIG. 14 is a perspective view of one side plate of a retractor in accordance with another embodiment of the invention.

In yet another aspect, as shown in association with a side plate 180 in FIG. 14, retractor 150 may include a sleeve 200. The distal end portion 174 of the side plate 180 is inserted into a slip-cover portion 202 with is attached to a flexible sleeve 200 until the slip-cover portion 202 is positioned between the proximal end portion 168 and the distal end portion 174 of each blade portion 164 and 166. The flexible nature of the sleeve 200 allows the sleeve 200 to adapt to both straight and curved blade designs. It will be appreciated that this embodiment may equally apply to one or both of the selected blade portion(s) 164, 166.

An attached conduit 204 extends beyond the proximal end portion 206 of the sleeve 200 and includes a plug 208 upon the conduit's opposing end 210. The plug 208 allows the conduit 204 to be attached to a source 33 by which the sleeve 200 may act in a manner consistent with the at least one conduit described herein. That is, in operation, it is possible for the plug 208 to insert to any of the sources 33 described previously, including but not limited to a light guide, heat exchanger, vortex tube, or other device capable of producing a chilled fluid stream. Alternatively, it is possible that the sleeve include a first conduit 204 and a second conduit (not shown) such that each may connect to a separate source 33. It would be appreciated that a sleeve 200 having a first conduit 204, first plug 208 would connect to, for example, a light guide 30a while a second conduit (not shown) with a second plug (not shown) would connect to, for example, a heat exchanger, vortex tube, etc. In this manner, the sleeve 200 offers to the surgeon a manner by which the surgical site 12 may be both chilled and illuminated without compromising the access path within the bore 24.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in numerous combinations depending on the needs and preferences of the user.

What is claimed is:

1. A surgical access device comprising:
   a body member including at least a first substantially rigid blade portion having a wall, wherein the wall further includes an inner shell that is spaced apart from and removeably couples to an outer shell;

at least one conduit formed in the space between the inner and outer shells of the first blade portion for circulating a chilled fluid through the at least one conduit so as to cool tissue proximate the body member, wherein at least one rib extends from the inner shell and sealingly engages an inner wall of the outer shell to form the at least one conduit;

an external access port formed on a proximal end portion of the body member for inserting a chilled fluid through the at least one conduit;

an exhaust formed on the proximal end portion for removing the chilled fluid from the at least one conduit; and a cold source for chilling the fluid prior to circulating the fluid through the at least one conduit.

2. The device of claim 1 further comprising a second blade portion having a wall, wherein the wall includes a second inner shell that removeably couples to a second outer shell including at least one conduit formed between the inner and outer shells of the second blade portion for circulating a chilled fluid through the at least one conduit so as to cool tissue proximate the body member, wherein at least one rib extends from the inner shell and sealingly engages an inner wall of the second outer shell to form the at least one conduit in the second blade portion.

3. The device of claim 1 further comprising at least one side plate having at least one conduit formed therein and operatively coupled to the cold source.

4. The device of claim 1 wherein the inner shell comprises a material that allows for light transmission to a surgical site.

5. A method of thermally treating tissue during a surgical procedure, comprising:

making an incision in a patient's skin;

inserting a surgical access device into the tissue of the patient, wherein the surgical access device includes a body member having a first portion and a second portion wherein each of the first portion and the second portion includes a body member including at least a first substantially rigid blade portion having a wall, wherein the wall further includes an inner shell that is spaced apart from and removeably couples to an outer shell;

at least one conduit formed in the space between the inner and outer shells of the first blade portion, wherein at least one rib extends from the inner shell and sealingly engages an inner wall of the outer shell to form the at least one conduit;

an external access port formed on a proximal end portion of the body member for inserting a chilled fluid through the at least one conduit;

an exhaust formed on the proximal end portion for removing the chilled fluid from the at least one conduit; and a cold source for chilling the fluid prior to inserting the fluid through the at least one conduit;

expanding the body member to move the first portion away from the second portion, creating pressure on the tissue; and circulating the chilled fluid through the conduit so as to cool tissue proximate the body member.

6. The method of claim 5, wherein circulating the chilled fluid further comprises circulating a liquid through the conduit.

7. The method of claim 5, wherein circulating the chilled fluid further comprises circulating a gas through the conduit.

8. The method of claim 5, wherein the chilled fluid has a temperature between the range of approximately 10° C. and approximately 30° C.

9. The method of claim 5, further comprising:

recirculating the fluid through the cold source to establish a closed loop system.

10. The method of claim 9, further comprising:

supplying the fluid through the cold source to the body member and through the conduit to the exhaust.

11. The method of claim 5, wherein the surgical access device further comprises at least one side plate having a conduit formed in the wall thereof, the method further comprising:

circulating chilled fluid through the conduit in the at least one side plate so as to cool tissue proximate the at least one side plate.

12. The method of claim 5, further comprising:

supplying light to at least one of the first portion and the second portions, wherein the light passes from at least one of the first portion and the second portion.

* * * * *